United States Patent [19]

Pliura et al.

[11] Patent Number: 5,770,727
[45] Date of Patent: Jun. 23, 1998

[54] CROSSLINKED HEMOGLOBIN PRODUCT COMPRISING TETRAMERIC AND OLIGOMERIC HEMOGLOBIN UNITS

[75] Inventors: Diana Pliura, Mississauga; Lawrence T. Wong, North York; Song Swee Er, Scarborough, all of Canada

[73] Assignee: Hemosol Inc., Etobicoke, Canada

[21] Appl. No.: 672,868

[22] Filed: Jun. 28, 1996

Related U.S. Application Data

[63] Continuation of Ser. No. 231,945, Apr. 21, 1994, Pat. No. 5,532,352, which is a continuation-in-part of Ser. No. 31,830, Mar. 16, 1993, abandoned.

[51] Int. Cl.[6] ................ C07D 487/22; C07K 15/22
[52] U.S. Cl. ................ 540/145; 530/385; 514/6
[58] Field of Search ................ 530/385; 514/6; 540/145

[56] References Cited

U.S. PATENT DOCUMENTS

| | | | |
|---|---|---|---|
| 4,529,719 | 7/1985 | Tye | 530/385 |
| 4,822,877 | 4/1989 | Inada et al. | 540/145 |
| 4,857,636 | 8/1989 | Hsia | 530/385 |

OTHER PUBLICATIONS

J. Courtois et al. A. Wickstrom. Action de l'acide periodique sur les tri et tetraholosides non reducteurs. I. Etude de raffinose. Bull. Soc. Chim. Biol. 32, 759 (1950).

A.K. Mitra & A.S. Perlin. The Configuration of Glycoside Linkages in Oliogosaccharides. V. The Sucrose Linkage in Raffinose and Stachyose, Can. J. Chem. 35, 1079 (1957).

Perlin. Glycol–cleavage Oxidation. In "The Carbohydrate–Chemistry and Biochemistry" 2nd Edition, Ed. W. Pigman and D. Horton. vol. 1B. Academic Press, 1980, p. 1167.

G.L. Moore et al. Molecular Weight Determinations of O–Raffinose–Polymerized Human Hemoglobin Biomat. Art Cells & Immob. Biotech. 20, 293 (1992).

J.C. Hsia et al. Pharmacokinetics Studies in the Rat on O–Raffinose Polymerized Human Hemoglobin Biomat., Art Cells & Immob. Biotech. 20 587 (1997).

Chang & Varman, Effects of a Single Replacement of One of Ringer Lactate Hypertonic Saline/Dextran, 7g% Albumin . . . Biomat., Art. Cells & Immob. Biotech 20, 503 (1992).

Vogel et al. Effects of O–Raffinose–Polymerized Human Hemoglobin on Coronary tone and Cardiac Function in Isolated Hearts. Biomat. Art. Cell 1& Immob. Biotech 20, 673 (1992).

Keipert et al. The Role of the Kidneys in the Excretion of Chemically Modified Hemoglobins., Biomat., Art. Cells & Immob. Biotech. 20, 737 (1992).

Kluger et al. Biochemistry., 1992, 31, 7551–9.

*Primary Examiner*—Mukund J. Shah
*Assistant Examiner*—Pavanaram K. Sripada
*Attorney, Agent, or Firm*—Ridout & Maybee

[57] ABSTRACT

A chemically modified, crosslinked hemoglobin product suitable for use as a hemoglobin based oxygen carrier comprises a mixture of hemoglobin species and consists essentially of about 40% tetrameric hemoglobin units of molecular weight about 64,000 daltons, up to 5% dimeric hemoglobin units of molecular weight about 32,000 daltons, and the balance oligomeric hemoglobin units of molecular weight up to about 60,000 daltons, the mixed product containing no polymeric hemoglobin species of molecular weight greater than 600,000 daltons. The product can be made directly by a crosslinking reaction under controlled conditions, without the need for separating therefrom high molecular weight species.

3 Claims, 3 Drawing Sheets

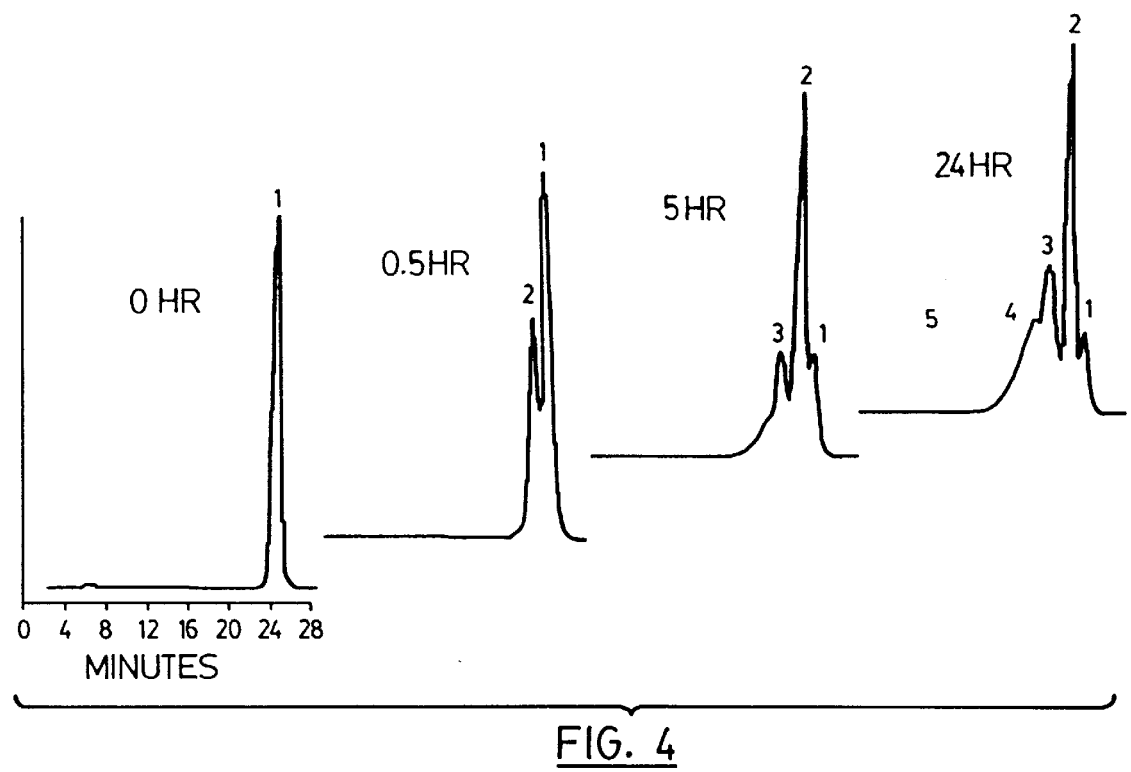
FIG. 4
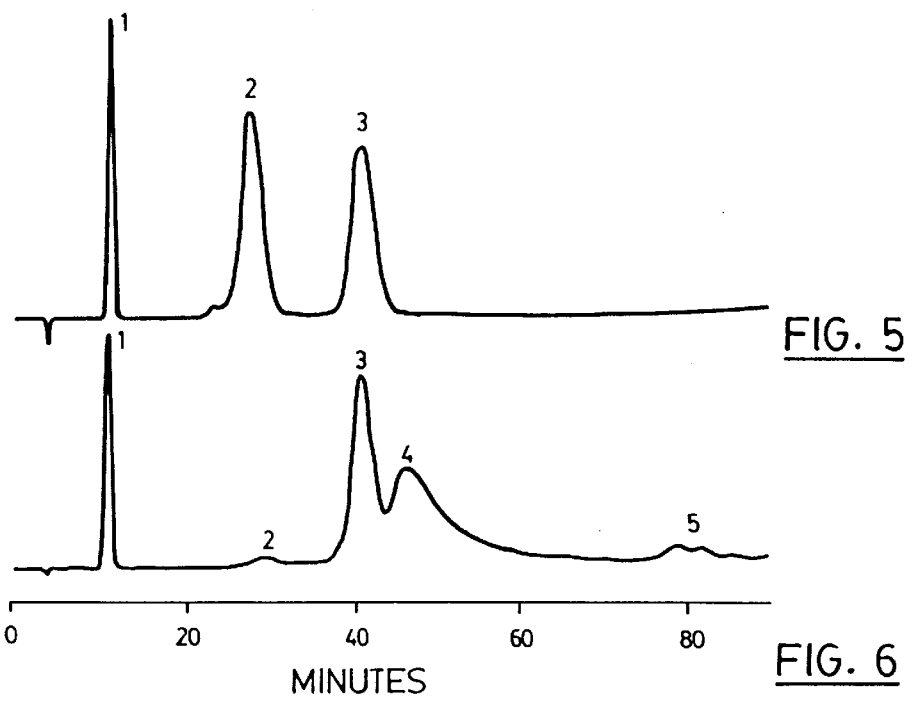
FIG. 5
FIG. 6 with polyaldehydes. The particular
CROSSLINKED HEMOGLOBIN PRODUCT COMPRISING TETRAMERIC AND OLIGOMERIC HEMOGLOBIN UNITS This is a continuation of U.S. patent application Ser. No. 08/231,945, filed Apr. 21, 1994, U.S. Pat. No. 5,532,352 which is in turn a continuation-in-part of application ser. No. 08/031,830 filed Mar. 16, 1993, now abandoned.

FIELD OF THE INVENTION

This invention relates to blood substitutes and processes for their preparation. More specifically, it relates to blood substitutes based on hemoglobin, and processes for the chemical modification of hemoglobin to improve its suitability for use as the basis of a blood substitute.

BACKGROUND OF THE INVENTION

Hemoglobin, as the natural oxygen transporter component of blood, is an obvious candidate to form the basis of a blood substitute, e.g. as an aqueous solution. Extensive scientific work has been done and reported, on attempts to provide a satisfactory hemoglobin solution to act as a blood substitute. The chemical properties of hemoglobin outside the red blood cells are, however, markedly different from its properties inside the red blood cells, e.g. as regards its oxygen affinity. The need for some form of chemical modification of hemoglobin to render it suitable for use as a blood substitute has long been recognized and has been quite extensively investigated.

It is well known that hemoglobin comprises a tetramer of four sub-units, namely two $\alpha$ sub-units each having a globin peptide chain and two $\beta$ sub-units each having a globin peptide chain. The tetramer has a molecular weight of approximately 64 kilodaltons, and each subunit has approximately the same molecular weight. The tetrameric hemoglobin in dilute aqueous solution readily dissociates into $\alpha$-$\beta$ dimers, and even further under some conditions to $\alpha$-sub-unit monomers and $\beta$-sub-unit monomers. The dimers and monomers have too low a molecular weight for retention in the circulatory system of the body, and are filtered by the kidneys for excretion with the urine. This results in an unacceptably short half life of such a product in the body. Moreover, uncrosslinked hemoglobin induces significant nephrotoxicity, so that there is a need to minimize the concentration of uncrosslinked hemoglobin in the products. The need for chemical bonding between the sub-units to ensure the maintenance of the tetrameric form ("intramolecular crosslinking") has previously been recognized. Also, the linking together of two or more tetrameric units to form hemoglobin oligomers and polymers of molecular weight greater than 64 kilodaltons ("intermolecular crosslinking") has also been recognized as desirable in many instances.

When present in the red blood cells, hemoglobin is bound to a natural ligand, diphosphoglycerate (DPG) at a particular site in the hemoglobin molecule known as the DPG cleft or pocket. When the red blood cell membrane is removed, the DPG dissociates from the hemoglobin, with consequent steric rearrangement of the hemoglobin molecule and consequent undesirable increase in the affinity of the hemoglobin for oxygen. A satisfactory blood substitute based on hemoglobin should be capable of binding, transporting and releasing oxygen largely in the same manner and under the same conditions as hemoglobin present in natural whole blood. This problem has been addressed in the past by covalently attaching DPG-analogs such as pyridoxal-5'-phosphate PLP to hemoglobin to form the basis of a blood substitute.

BRIEF REFERENCE TO THE PRIOR ART

U.S. Pat. No. 4,857,636 Hsia, issued Aug. 15, 1989, describes a blood substitute based on chemically modified hemoglobin, in which the hemoglobin is intramolecularly crosslinked by reaction with polyaldehydes. The particular polyaldehydes recommended for use in the Hsia patent are the products of ring opening oxidation of saccharides such as raffinose, a trisaccharide. The reactions are said to bind the hemoglobin sub-units into tetramers by non-site specific crosslinking of the globin chains of the sub-units to one another, to stabilize the tetrameric hemoglobin in the T-configuration or the R-configuration for control over the oxygen affinity of the resultant tetramer. The reactions are also said to be controllable to allow the formation of oligomers of hemoglobin by intermolecular crosslinking in predetermined amounts along with the stabilized tetramer. Non-site specific crosslinking of the globin chains according the Hsia patent is taught therein to be advantageous in allowing the use of large molar excesses of polyaldehyde for enhanced yields of crosslinked, stabilized hemoglobin, as opposed to site specific crosslinking where stoichiometric quantities of reagents are usually necessary.

Further studies and investigations of the processes and products disclosed in the Hsia patent have revealed, however, that by variation of some of the conditions of reaction and other factors, unexpected improvements in the control and reproducibility of the process, and in the nature and consistency of the end products, can be achieved. A product such as a blood substitute, intended for administration to live animals, should have a controllable and reproducible composition of components, so that its efficacy and side effects can be properly monitored.

SUMMARY OF THE INVENTION

It is an object of the present invention to provide novel processes for preparing blood substitutes based on hemoglobin.

It is a further object of the present invention to provide improved methods and conditions of reacting hemoglobin with polyaldehydes derived from the oxidative ring opening of saccharides.

The present invention is based to some extent upon the discovery that the polyaldehyde product of the oxidative ring opening of a di/tri-saccharide (this term being used herein to denote disaccharides and trisaccharides) is highly specific in reacting with specific sites in the 2,3-diphosphoglycerate binding (DPG) cleft of hemoglobin, to crosslink two $\beta$-globin chains thereof, provided that the polyaldehyde product itself is substantially homogeneous. Ring-opened, oxidized di/tri-saccharides undergo hydrolytic degradation under alkaline conditions. Solutions of ring-opened, oxidized raffinose (o-raffinose), for example, stored at pH>7 undergo significant alkaline hydrolysis to provide oxidized disaccharides (e.g.o-sucrose) and oxidized monosaccharides (e.g. o-galactose) ,in admixture with the oxidized trisaccharide. Stabilization of o-raffinose solutions is achieved by maintaining stock solutions at pH<7, and preferably pH<6.

The process of the present invention, however, prepares a substantially homogeneous polyaldehyde by maintaining the pH of ring-opened, oxidized di/tri-saccharide solutions such as raffinose at pH 5.0–7.0. This product can be reacted with hemoglobin at a stoichiometry (based on moles of di/tri-saccharide to tetramers of hemoglobin) of about 1:1–4:1, to give high yields of crosslinked, stabilized hemoglobin product. The very large excesses of crosslinking reagent recommended in the aforementioned Hsia patent for obtaining high yields of products, of 20:1 and thereabouts, turn out to be unnecessary. Moreover, the side effects experienced in using such large excesses of crosslinking reagent, namely lack of control and reproducibility of the nature of the composition of the resulting crosslinked product, are largely avoided. Formation of high molecular weight aggregates are avoided by using limited stoichiometry of crosslinking reagent.

Thus, according to one aspect of the present invention, there is provided a process of chemically modifying hemoglobin to render it more suitable for use as a blood substitute in aqueous solution, which comprises:

(a) subjecting a di/tri-saccharide to an oxidative ring opening process to produce a polyaldehyde therefrom;

(b) adjusting and maintaining the pH of the resulting product solution to a value within the range from about pH 5.0 to pH 7.0, so as to prevent any substantial hydrolytic degradation of the polyaldehyde so formed;

(c) reacting the product of process step (b) with hemoglobin in solution, at a stoichiometric ratio, based upon di/trisaccharide and hemoglobin tetramers, of from about 1:1–4:1;

(d) reducing the Schiff base linkages so formed to secondary amine linkages; and (e) recovering the modified hemoglobin so formed.

The nature and composition of the crosslinked product obtainable by use of the present invention is not only controllable and reproducible, but also advantageous. The product contains little unmodified hemoglobin, and what little there is can if necessary readily be removed by diafiltration. It is free from high molecular weight (greater than 600,000 daltons) hemoglobin aggregates. It consists essentially of about 40% tetrameric hemoglobin, less than 5% of dimeric hemoglobin, with the balance being oligomers with molecular weights between 64,000 and 500,000

It has previously been thought necessary to avoid crosslinking of hemoglobin at pH below 7.4, for fear of excess formation of methemoglobin. A further unexpected and advantageous feature of the present invention is that, with the crosslinking reagents described herein, hemoglobin crosslinking reactions can be conducted within the pH range 5.0–7.0 without excessive formation of methemoglobin. This is of course the pH range within which the o-saccharide (polyaldehyde) is maintained for stability, so that an extra process step of pH adjustment or the like, prior to the crosslinking reaction, is advantageously avoided.

BRIEF REFERENCE TO THE DRAWINGS

FIG. 4 is a diagrammatic presentation of the kinetics of the reaction described in Example 3 below;

FIG. 5 is a chromatogram illustrating the C4 globin chain analysis of unmodified hemoglobin from Example 4 below, showing heme, beta chain and alpha chain;

FIG. 6 is a chromatogram similar to FIG. 5, illustrating the C4 globin chain analysis of crosslinked h emoglobin from Example 4 below.

DESCRIPTION OF THE PREFERRED EMBODIMENTS

The preferred di/tri-saccharide for use in the present invention is the trisaccharide raffinose, and so the invention will be further described, for reasons of clarity, with specific reference to the use of raff inose. It is to be understood, however, that this i s a preferred c hoic e of di/tri-saccharide, and the inven tion is not to be construed as limited thereto. Other suitable trisaccharides include planteose, manninotriose, galactotriose, gentianose, melezitose, o-alpha-D-galactopyranosyl-(1-6')-mannobiose, maltotriose and cellotriose. Suitable disaccharides include sucrose, lactose, maltose, isomaltose, cellabiose, melibiose, planteobiose, galactobiose, gentiabiose, turanose and mannobiose. The invention is not to be construed as limited to the use of the specifically mentioned di/tri-saccharides.

Preferably, the raf pfinose is oxidatively ring opened, by reaction in solution with a strong oxidizing agent such as a periodate, for example sodium periodate or potassium periodate. This oxidation takes place at very low pH. After the reaction has been conducted, the solution is adjusted to pH 5.0–7.0 by suitable buffering, preferably to 6.0–6.5. Any salts formed as a result of the pH adjustment, which might interfere with the subsequent reactions with hemoglobin, are preferably removed at this stage, e.g. by crystallization, mixed bed ion exchange, gel permeation chromatography, reverse osmosis, etc. Phosphate buffers are effective but are preferably avoided, because residual phosphate ions in the solution can interfere with the subsequent cross-linking reaction. The resulting product can be stored, in aqueous solution, preferably buffered to about pH 6.0, ready for use. Suitable buffers are those which buffer to a pH range 6–7, and include MES (2-[N-morpholino]ethane sulphonic acid); BIS-TRIS (bis[2-hydroxyethyl ]imino-tris[hydroxymethyl] methane; ADA (N-[2-acetamido ]-2-iminodiacetic acid; ACES (2-[(2-amino-2-oxoethyl )-amino]ethanesulfonic acid); PIPES (piperazine-N ,N'-bis[2-ethanesulfonic acid]); MOPSO (3-[N-morpholino]-2 -hydroxypropanesulfonic acid); BIS-TRIS PROPANE (1,3-bis [tris(hydroxymethyl)-methylamino propane); BES (N,N-bis[2-hydroxyethyl ]-2-aminoethane sulfonic acid); MOPS (3-[N-morpholino ]propanesulfonic acid); TES(N-tris[hydroxymethyl] methyl-2-aminoethane sulfonic acid); HEPES (N-[2-hydroxy-ethyl ]piperazine-N'-[2-ethanesulfonic acid]), with BIS-TRIS and BIS-TRIS PROPANE most preferred.

Phosphate buffering of the raffinose reaction solution is also best avoided on grounds of efficiency of reaction. On subsequent crosslinking of the hemoglobin with the ring opened raffinose polyaldehyde product, the crosslinking reagent reacts specifically at the DPG binding site, but the phosphate would also interact at such a site. Accordingly, avoidance of phosphate avoids the reaction competition between the species, resulting in greater yields, faster reaction and better control over the resulting chemical products.

Figure 1:
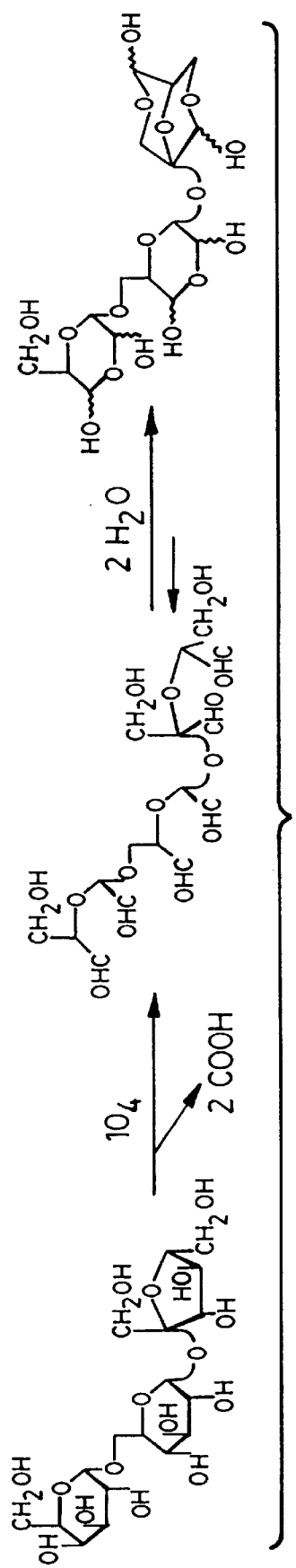
FIG. 1 is a diagrammatic representation of the chemical reaction of oxidative ring opening of raffinose to produce a hexa-aldehyde, and the subsequent chemical equilibrium formation with the acetal compound.

The chemical progress of this reaction is diagrammatically illustrated in FIG. 1 of the accompanying drawings. If the pH is not properly controlled, the o-raffinose partially hydrolyses to form a mixture of o-sucrose and o-galactose, and under some conditions to smaller oxidized fragments. The resulting product mixture of dialdehydes and tetraaldehydes is not only an undesirable mixture on grounds of its non-homogeneity and nonreproducibility, but also is less reactive towards the hemoglobin, thereby requiring the use of greater quantities for good yields of product. Crosslinking of hemoglobin with o-sucrose is effective and useful within the scope of the present invention, but takes place more slowly, and with different specificity than in the case of o-raffinose.

The hemoglobin for use in the process of the present invention is preferably human hemoglobin, derived from red blood cells. However, the invention is applicable also to other types of hemoglobin to form the basis of a blood substitute, such as animal hemoglobins especially bovine hemoglobin, ovine hemoglobin and the like. Human hemoglobin is currently the preferred choice, to form the basis of a blood substitute for administration to human patients.

The hemoglobin can be recovered and prepared for use in the present invention according to standard, known techniques. Thus, red blood cells are lysed, and cellular debris and stroma are removed therefrom by standard techniques of centrifugation, filtration and the like. Preferably, a solution of hemoglobin with a concentration of 2–14% by weight of hemoglobin is used, to yield a product having the most desirable composition and combination of properties. The purity of the hemoglobin should be as high as practically achievable, to avoid toxicity in the final product. Final purification suitably takes place chromatographically.

Hemoglobin can naturally exist in the tight (T) conformation as normally assumed by deoxyhemoglobin, or in the relaxed (R) conformation as normally assumed by oxyhemoglobin. The oxygen binding characteristics of deoxyhemoglobin are the more desirable characteristics, since this is the conformation naturally assumed by the hemoglobin inside the natural red blood cells of the blood. It is accordingly preferred to effect the process of the present invention on deoxyhemoglobin, the crosslinking reaction with the polyaldehyde derived from ring opening of raffinose serving to stabilize the hemoglobin in the T-configuration. If, however, one chooses for any reason to start with R-configuration hemoglobin, the crosslinking reaction according to the invention stabilizes the hemoglobin into the R-configuration throughout.

Deoxygenation of hemoglobin to form deoxyhemoglobin is preferably conducted, prior to the reaction with the crosslinking agent, by subjecting the hemoglobin solution to treatment with a non-oxygenating gas such as nitrogen, according to known techniques. Some prior art processes, including that described in the aforementioned Hsia patent, teach the use of a reducing agent such as sodium dithionite for removing the final traces of oxyhemoglobin. Such a technique is not preferred according to the present invention, since it has been found that the presence of dithionite residues inhibits the o-raffinosemediated oligomerization of the tetrameric hemoglobin units. It is thus preferred to continue the treatment with a stream of nitrogen, followed by appropriate degassing, for sufficiently long periods of time to effect complete conversion to deoxyhemoglobin in this manner.

Reaction of the deoxyhemoglobin aqueous solution with the polyaldehyde crosslinking reagent so formed suitably takes place in aqueous solution, at a temperature in the range of 4°–40° C., and for a period of time of from 2–96 hours, preferably about 24 hours. The reaction solution is buffered, preferably with a bis-tris buffer system, to a pH not exceeding 7.5 and preferably in the range 5.0–7.0 to avoid risk of hydrolysis and decomposition of the hexa-aldehyde. The molar ratio of polyaldehyde to hemoglobin is, as previously stated, in the range 1:1–4:1 on the basis of o-raffinose to hemoglobin tetramers, and preferably at a stoichiometry of about 2.5:1–3.5:1. The concentration of deoxyhemoglobin is suitably 1–15% (w/v) and preferably in the range 5–10% (w/v).

Figure 2:
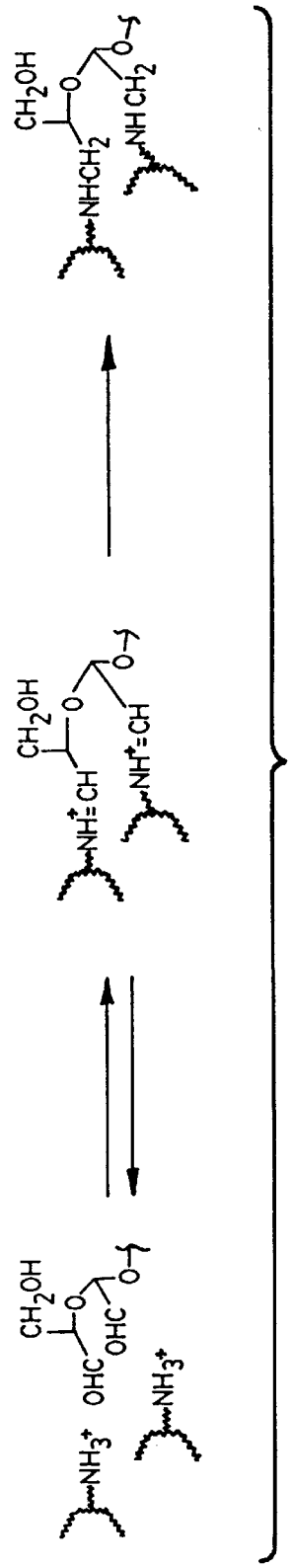
FIG. 2 is a diagrammatic representation of the chemical reaction of the polyaldehyde with hemoglobin and the subsequent chemical reduction step.

As a result of the reaction of the hemoglobin with the hexa-aldehyde, in which amino groups on the hemoglobin chain react with the aldehyde groups of the crosslinking reagent, a Schiff base linkage is formed which is a reversible linkage. The coupled product effectively enters into an equilibrium balance with the non-crosslinked hemoglobin and crosslinker. This is diagrammatically illustrated in FIG. 2 of the accompanying drawings. This linkage now needs to be reduced to a primary amine linkage, which is stable and irreversible, to complete the crosslinking of the hemoglobin for blood substitute purposes. The reducing agent is preferably added to the reaction mixture after the substantial completion of the crosslinking reaction. Whilst the prior art, for example the aforementioned Hsia patent, recommends the use of sodium borohydride as the reducing agent, there is used according the preferred aspect of the present invention borane dimethylamine as the reducing agent. This has the significant advantage over the prior art of avoiding generation of gaseous hydrogen, which occurs when sodium borohydride is used, and leads to difficulties in control and general conduct of the process. The use of borane dimethylamine is a significant improvement in this regard. Other water soluble borane lower alkyl amine reducing agents including but not limited to borane-tert-butylamine, borane-ammonia; borane-dimethylamine; borane-trimethylamine; and borane triethylamine, can also be used. Another useful but less preferred reducing agent is sodium cyanoborohydride.

Reduction of the Schiff bases formed during the crosslinking and reduction of unreacted aldehyde groups must suitably takes place in aqueous solution at a temperature range of 2°–25° C., for a period of time from 2–36 hours, preferably 24 hours. The reaction mixture is suitably buffered to pH 5–8, preferably to 6.5–7.0. The molar ratio of reducing agent to the sum of imine and aldehyde groups is in the range 2:1 to 5:1, preferably 2.5:1 to 3.5:1 based on the stoichiometry of reducing agent to aldehyde groups added to initiate crosslinking.

After the stabilization of the crosslinked product by reduction with dimethylamine borane has been completed, the product is suitably treated with carbon monoxide to form a protected complex of hemoglobin, for storage purposes. After treatment with carbon monoxide, which conveniently takes place by passing carbon monoxide into the reaction solution so formed at the temperatures of reaction, the mixture is preferably diafiltered appropriately to remove residual reducing agent and any other reagent residues. Residual buffer can be removed by gel permeation chromatography. If necessary in order to remove uncrosslinked hemoglobin residues, magnesium chloride can be added to dissociate the uncrosslinked tetrameric hemoglobin, followed by diafiltration for removal of the residues. The resulting material is then ready for storage under sterile conditions until use.

DETAILED DESCRIPTION OF THE MOST PREFERRED, SPECIFIC EMBODIMENTS

The invention will be further illustrated by reports of specific, non-limiting examples, as below:

EXAMPLE 1

Preperation of Periodate Oxidized Raffinose

To a solution of raffinose (76 gm, 0.128 mole) in sterile water (1 litre), cooled to 4°–10° C. on an ice bath, solid sodium-m-periodate (181 gm) was added in aliquots and the temperature maintained at <15° C. by adjusting the rate of addition and cooling in an ice bath. After the final addition of sodium-m-periodate, the solution was maintained at 10°–15° C. and stirred for 2–24 hours for completion of the oxidation reaction. The solution was then cooled to 4° C. and excess periodate was then neutralized by the controlled addition of sodium bisulphite. The pH of the solution was then adjusted with 10 N NaOH (100 ml), solid Bis-Tris (to a final concentration of 20 mM). was added and the pH carefully adjusted to 5.0. The solution was partially desalted by storing at 4° C. for 16–24 hours to induce crystallization and the clear supernatant, containing the oxidized raffinose, was decanted and filtered. The final pH of the solution was carefully adjusted to 5.9+/−0.1.

Figure 3:
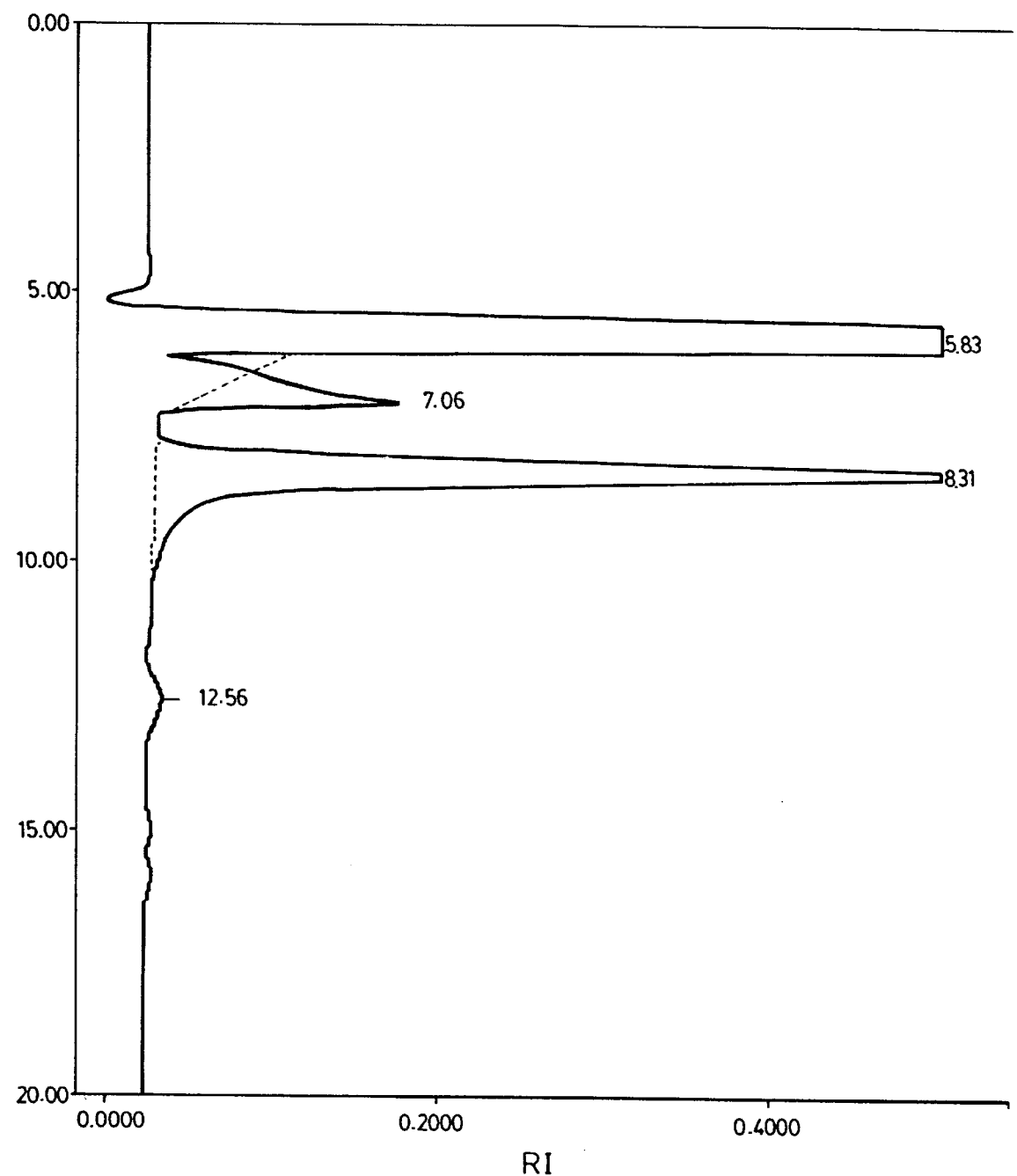
FIG. 3 is the HPLC analysis curve of the product of Example 1 described below.

The HPLC analysis of the product of the above process, taken after storage of the reaction solution at pH 6.0 for 21 hours, is presented in FIG. 3. The presence of only a single peak relating to ring-opened saccharide products, namely the hexa-aldehyde o-raffinose, is noteworthy, and indicates homogeneity of the product and absence of alkaline hydrolysis products. The only other significant peaks on the chromatogram pertain to salts and formic acid, which are readily removable.

The o-raffinose may be purified further by desalting on using a) ion exchange mixed bed resins b) size exclusion chromatography or c) reverse osmosis.

EXAMPLE 2

Purification of O-Raffinose by mixed Bed Ion Exchange Chromatography

A solution of o-raffinose (20 ml, pH 5.65) was adjusted to pH 1.6 by dropwise addition of 6 N HCl and then the solution was passed through 30 mL of Biorad AG 501-8 (D) analytical grade mixed bed resin. The eluent was collected and purified sample lyophilized to provide a solid, white crystalline product.

EXAMPLE 3

Modified Method for cccControlling cross linking of Hemoglobin by O-Raffinose followed by Reduction with Dimethylamine Borane A 30 mL solution of purified human hemoglobin (8% w/v) in 50 mM Bis-Tris buffer at pH 6.5 was converted to deoxyhemoglobin under a stream of moisturized nitrogen gas for approximately 4–6 hours at room temperature with constant stirring. The ring-opened, oxidized raffinose (112.5 $\mu$moles) was degassed and added to initiate the cross-linking and oligomerization reactions. After 24 hours, 3 M sodium acetate was added to provide a final concentration of 30 mM and then followed by reduction with 2.25 mmole of dimethylamine borane dissolved in 1.3 ml of degassed water. The reduction was allowed to proceed overnight.

The progress of the reaction was monitored by HPLC, and the results are presented diagrammatically on FIG. 4. Peak no. 1 derives from hemoglobin dimeric sub-units (32 kdaltons) present in the mixture—clearly they are few in number. Peak no. 2 derives from the tetrameric (64 kdalton) crosslinked hemoglobin constituting about 40% proportion of the product mixture. Peak no. 3 derives from dimerized (128 kdalton) and peak no. 4 derives from oligomeric hemoglobin units of average molecular weight about 380 kdaltons. It is to be noted that the product mixture contains no fraction of higher molecular weight higher than 600 kdaltons.

EXAMPLE 4

Demonstration of the Specificity of the Crosslinking Step

To monitor the progress of the crosslinking reaction, o-raffinose:Hb solutions were reduced with dimethylamine borane, in the presence of sodium acetate, after cross-linking for 1 hr, 2.5 hr and 23 hrs. The stabilized cross-linked 64 kD fractions were isolated by preparative size exclusion chromatography on a Superdex (Pharmacia) gel permeation using a mobile phase of 0.5 M magnesium chloride.

The effect of the magnesium chloride solution is to dissociate the uncrosslinked tetrameric hemoglobin into alpha-beta dimers (32 kdalton). Magnesium chloride does not dissociate crosslinked hemoglobin. In this way, crosslinked hemoglobin can be separated from uncrosslinked hemoglobin for analysis purposes.

The heme and globin chains of the cross-linked 64 kD species were separated by reverse phase HPLC using 330 angstrom pore size C4 Vydac columns (250×4.6 mm for analytical and 250×10 mm for preparative; The Separations Group, Hesperia CA) and developers containing 0.1% trifluoroacetic acid and various gradients of acetonitrile starting at 38% and ending at 60% were employed to effect separation. The effluent was monitored at 220 nm and the globin chains recovered from the effluent by lyophilization.

In a similar manner, the heme and the globin chains of the uncrosslinked, unmodified hemoglobin were separated.

FIG. 5 of the accompanying drawings shows the reverse phase globin chain chromatography for the unmodified hemoglobin, and FIG. 6 shows that for the modified, crosslinked hemoglobin. In each case, as will be readily recognizable to those familiar with hemoglobin analysis, and as readily deducible from reference publications thereon, peak 1 represents heme, peak 2 represents unmodified beta-globin chains, peak 3 represents unmodified alpha-chains, peak 4 represents predominantly modified beta-dimers and peak 5 represents predominantly modified alpha-dimers. By comparison of FIGS. 5 and 6, one can readily see that crosslinking according to the present invention takes place specifically on the beta-dimers, i.e. in the beta-chains of the hemoglobin tetrameric units.

To determine the specific position of the modification (crosslinking), the globin chains represented by peak (fraction) 2 on FIG. 5, peak (fraction) 3 and peak (fraction) 4 on FIG. 6 were submitted to enzymatic hydrolysis using trypsin, followed by peptide analysis, as follows.

Enzimatic Hudrolysis of Globin Chains

Isolated, globin chains were first dissolved in 8 M urea (to increase susceptibility to hydrolysis) and kept at room temperature for 2–4 hours. The solution was diluted to 2 M urea with 90 mM ammonium bicarbonate buffer at pH 8.5. Trypsin (2% of total protein) was added and the solution was digested for 18–20 hours at room temperature. The tryptic hydrolysate was then heated in boiling water for 2 minutes, diluted to 1 M urea with 80 mM ammonium bicarbonate buffer and digested with endoproteinase Glu-C (1% of total protein) for another 18–72 hours at room temperature. The hydrolysates were centrifuged or filtered before injection onto the HPLC column.

Peptide Analysis

Peptide fragments were separated by reverse phase HPLC on Vydac C18 columns (25×0.46 cm, The Separations Group, Hesperia, Calif.). Separations were made using developers of 0.1% TFA and gradients of acetonitrile starting at 0% and ending at 100% over a period of 100 minutes. Eluent was monitored at 220 nm for detection of peptidyl fragments.

Trypsin specifically cleaves a protein chain at a lysine residue having a free primary amine group. It is specific in its reaction to primary amine groups which in hemoglobin can only derive from a lysine residue or a terminal amino acid group. The amino acid sequence of globin chains of hemoglobin is known. Thus, by peptide analysis of the tryptic digest, using reverse phase HPLC, on fraction 2 from FIG. 5 and fraction 4 from FIG. 6, it was shown that the crosslinking was specific to lysine-82 on the beta-chains, all of which were missing from the fraction 4 sample, and the terminal valine group from the beta-chain, half of which were missing from the fraction 4.

Lysine-82 on the beta-chains of hemoglobin is known from prior work to be located in the 2,3-diphosphoglycerate binding site of hemoglobin. Thus the specificity of crosslinking in the DPG binding site, using beta-lysine-82, by the process of the present invention, is demonstrated and established.

EXAMPLE 5

Preperation of the Periodate Oxidized Sucrose

The preparation was conducted according to the procedure described in Example 1 for periodate oxidized raffinose, using 3.8 gm (11.1 mmole) of sucrose dissolved in 50 ml of sterile water and 10.4 gm of solid sodium-m-periodate.

EXAMPLE 6

Controlled Ccrosslinking of Hemoglobin by O-Sucrose followed by Reduction with Borane Dimethylamine A 30 ml solution of purified human hemoglobin (8% w/v) in 50 mM Bis-Tris buffer at pH 6.5 was converted to deoxyhemoglobin under a stream of moisturized nitrogen gas for approximately 4–6 hours at room temperature with constant stirring. The ring-opened, oxidized sucrose .(115 mMoles) was degassed and added to initiate the crosslinking. After 24 hours, 3M sodium acetate was added to provide a final concentration of 30 mM. This was followed by reduction of the crosslinked product with 1.44 mMole of borane dimethylamine dissolved in 0.8 ml of degassed water. The reduction was allowed to proceed overnight.

We claim:

1. A chemically modified, crosslinked hemoglobin product comprising a mixture of hemoglobin species and consisting essentially of about 40% tetrameric hemoglobin units of molecular weight about 64,000 daltons, up to 5% dimeric hemoglobin units of molecular weight about 32,000 daltons, and the balance being oligomeric hemoglobin units of molecular weight up to about 600,000 daltons, the mixture containing no polymeric hemoglobin species of molecular weight greater than 600,000 daltons.

2. The hemoglobin product of claim 1 wherein the tetrameric and oligo i neric hemoglobin units have chemical crosslinks between respective beta globin chains at position lysine-82 in the diphosphorlverate site.

3. The hemoglobin product of claim 2, produced by crosslinking hemoglobin by reaction with 0-raffinose, followed by chemical reduction to secondary amine groups of the crosslinks so formed.

* * * * *